United States Patent [19]

Lund et al.

[11] Patent Number: 5,716,214
[45] Date of Patent: Feb. 10, 1998

[54] DENTAL PROSTHESIS

[75] Inventors: James Percy Lund; Jocelyne Feine, both of Senneville; Richard Taché, Outremont, all of Canada

[73] Assignee: Universite De Montreal, Montreal, Canada

[21] Appl. No.: 436,485

[22] Filed: May 8, 1995

[51] Int. Cl.$^6$ ................................................ A61C 8/00
[52] U.S. Cl. ................................................ 433/173; 433/182
[58] Field of Search ................................. 433/172, 173, 433/181, 182, 183, 193, 195

[56]  References Cited

U.S. PATENT DOCUMENTS

| | | | |
|---|---|---|---|
| 2,644,231 | 7/1953 | Brennan | 433/173 |
| 3,748,739 | 7/1973 | Thibert | 433/173 |
| 4,085,506 | 4/1978 | Lew | 433/173 X |
| 4,850,869 | 7/1989 | Steinfort et al. | 433/172 |
| 5,106,299 | 4/1992 | Ghalili | 433/172 |
| 5,234,341 | 8/1993 | Johansen | 433/172 |

*Primary Examiner*—Nicholas D. Lucchesi
*Attorney, Agent, or Firm*—Jacobson, Price, Holman & Stern, PLLC

[57]  ABSTRACT

A denture adapted to be locked in place in the mouth which includes the provision of two spaced-apart implanted pins in the gum with the pins being exposed and mounting spherical heads, each adapted to receive a rigid frusto-spherical seat member which is aligned and located in the artificial gum material of a denture such that the denture can be nested on the implant structure. The two implants and seat members have a locking device in the form of a sliding plunger extending tangentially to the frusto-spherical surfaces and a bore provided therein for interfering with the head of the implant when locked.

7 Claims, 3 Drawing Sheets

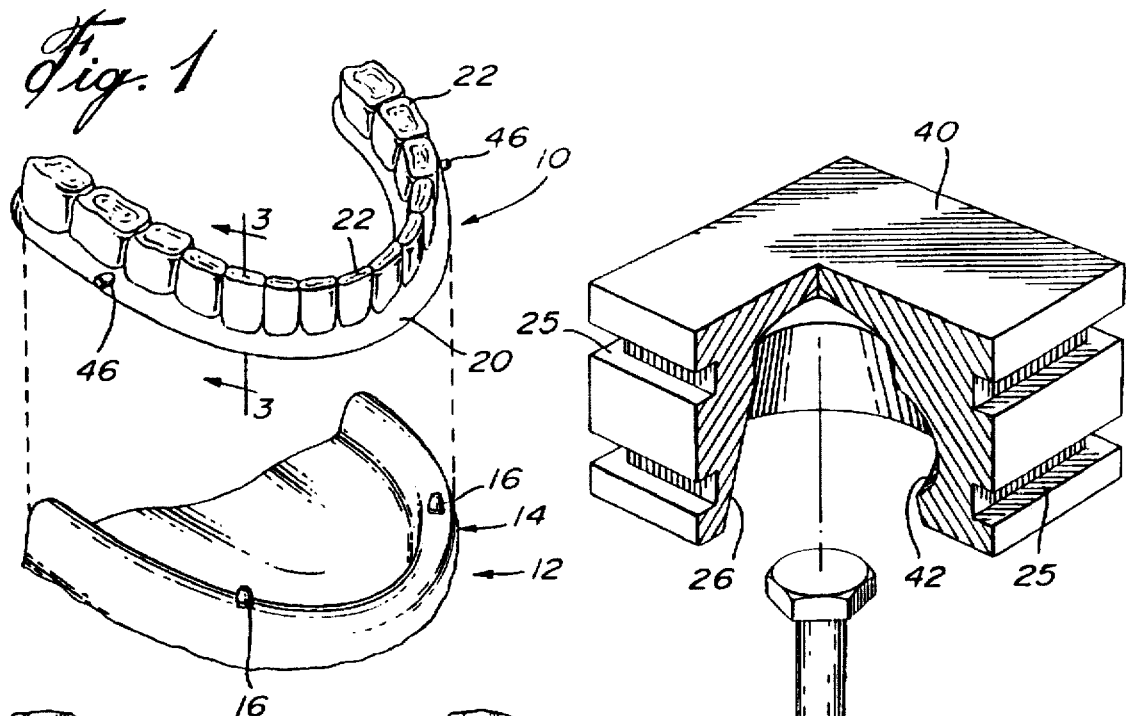
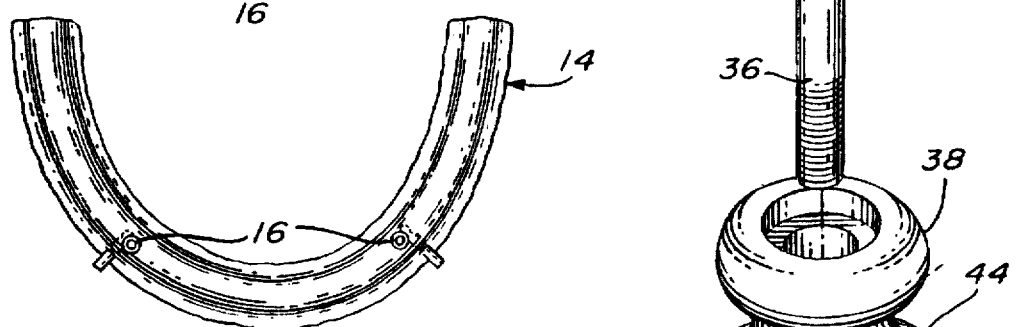
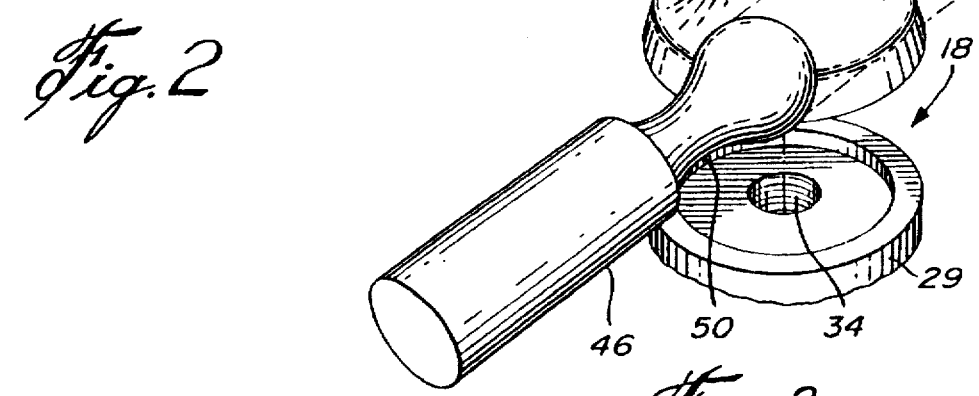

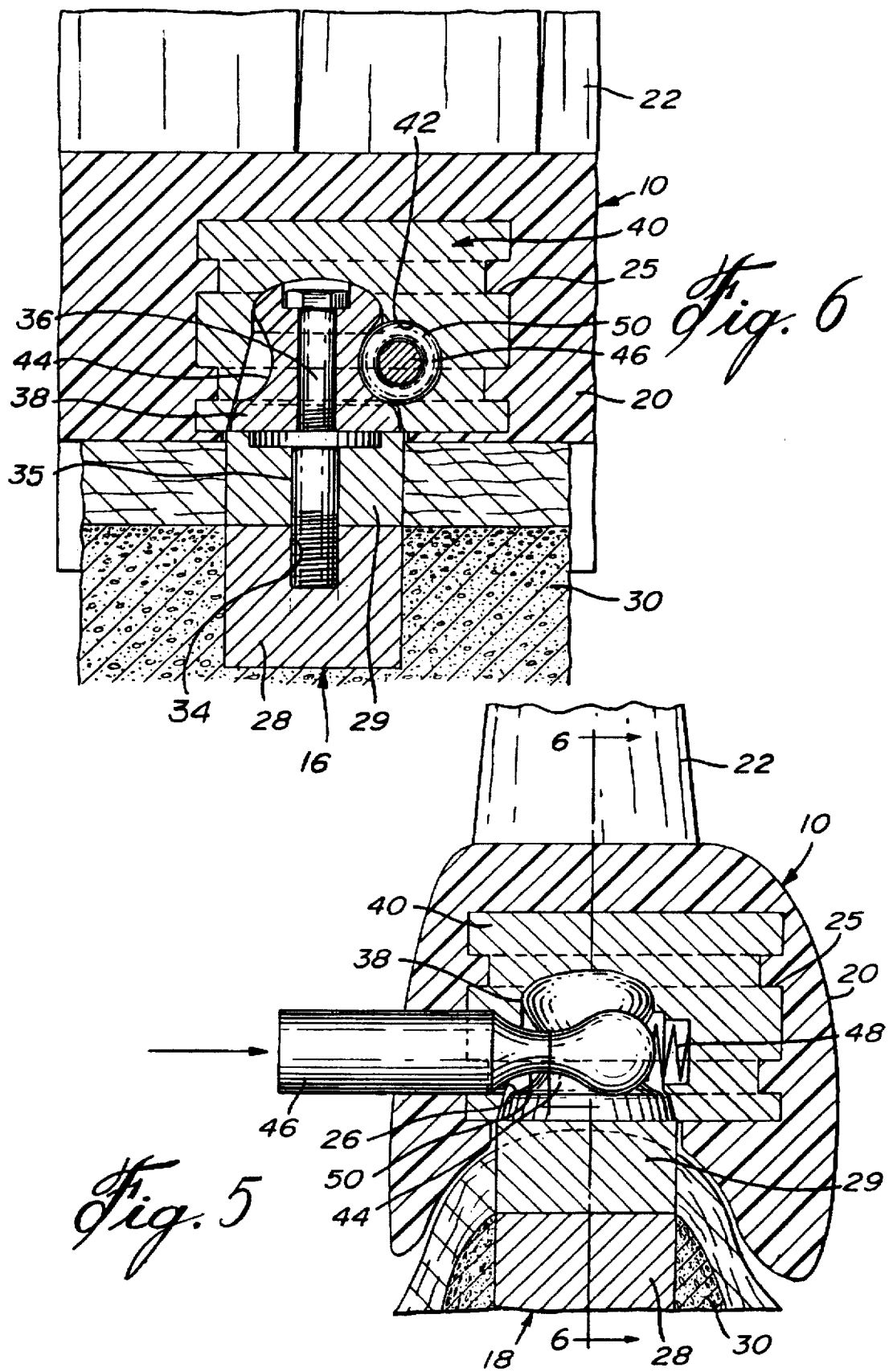

DENTAL PROSTHESIS

BACKGROUND OF THE INVENTION

1. Field of the Invention

The present invention relates to dental prostheses, and more particularly, to a denture detachably mounted to permanent endosseous implants.

2. Field of the Invention

It is known to provide permanently fixed dentures which include implants anchored in the mandible or maxilla osseous portions and a denture including an artificial gum and teeth structure being fixed to the implants and/or existing teeth or roots.

It is also known to provide a bridge or denture which includes a locking device adapted to lock onto the crown of a tooth. However, the torque which can be produced by the denture on the tooth or teeth by the function of the prosthesis can damage the crown of the tooth and render it useless.

It is also known to have a denture which is removably detached from an implant structure, wherein the implant structure includes a metallic arch or bar formed to bridge individual roots or root substitutes, such as pins implanted directly into the osseous material of the mandible or maxilla. The denture includes an artificial gum structure adapted to fit snugly over the arch and locking device for locking the denture to the arch. An example of such a device is described in U.S. Pat. No. 4,085,506, issued Apr. 25, 1978 to Isaih Lew. Such an assembly requires the arch to accommodate the locking device.

Canadian laid open Patent application No. 2,007,586 published May 7, 1991 by Richard H. Taché et al. describes a plurality of implant abutments, that is at least three, with the denture being rigidly locked thereon.

SUMMARY OF THE INVENTION

It is an aim of the present invention to provide an improved dental prosthesis which can be positively locked in place within the mouth on endosseous implants and which can be removed for cleaning, or to relieve emotional stress resulting from wearing a fixed prosthesis and to promote better esthetics and phonetics.

It is a further aim of the present invention to provide a dental prosthesis which is mounted on endosseous implants and includes a locking device to lock the prosthesis to the implants but which allows some of the forces of mastication to be transmitted to soft tissues.

It is a further aim of the present invention to provide an improved locking device for locking a denture on the two endosseous implants.

It is a further aim of the present invention to provide a simple denture which is removed and replaced in the mouth with a retaining device with maximum releasability.

A construction in accordance with the present invention comprises a prosthesis kit having two pins adapted to be implanted in the anterior regions of the bone of at least one of the mandible or maxilla whereby the implanted pins define a line of anterior/posterior rotation. The pins include axially opposed ends with at least one end to be exposed from the gum and having a circular cross-section and defining a male member which is at least frusto-spherical. A dental prosthesis is provided which includes an artificial gum and teeth extending from the artificial gum. Two separate rigid seat members are adapted to be embedded in the artificial gum of the prosthesis and each includes a body defining a frusto-spherical female seat adapted to receive the exposed male member of the pins. The seat members are adapted to be placed, in the artificial gum of the prosthesis, in alignment with the implanted pins such that when the prosthesis is fitted in the mouth onto the implanted pins, the seats will sit on the exposed male members. Locking means are provided within the two seat members and are adapted to coact with respective implanted pins.

In a more specific embodiment of the present invention, the locking means includes a slidable resiliently urged plunger in the seat member adapted to intersect the frusto-spherical female seat in a tangential axis, and a corresponding groove is defined in the respective frusto-spherical male member at the end of the pin such that the sliding member can slide in the groove in the pin when the prosthesis is installed so as to lock or unlock the prosthesis to the respective implanted pins, while allowing rotation.

A method is provided for a mechanical attachment of a denture to either the mandible or maxilla which includes providing two spaced-apart implants in the gum defining a line of rotation with each implant having an exposed male member of frusto-spherical shape, selecting two rigid seat members which match with the respective male members of the implants, preparing a denture by taking an imprint of the gum with the implants, embedding the seat members in the denture artificial gum material such that each respective seat member is aligned and is adapted to sit on the exposed male member of each implant and ensuring that the two implants and seat members have locking means for securing the denture to the implant structure.

One of the advantages derived from the method is that the implants can be located without the necessity of a template.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is an exploded fragmentary perspective view of the present invention;

FIG. 2 is a fragmentary top plan view of a detail of the invention shown in FIG. 1;

FIG. 3 is a fragmentary exploded view of another detail of the present invention;

FIG. 5 is a vertical gingival cross-section of the detail shown in FIG. 4;

FIG. 6 is a vertical cross-section, taken along line 6—6 of FIG. 5; and

DESCRIPTION OF THE PREFERRED EMBODIMENTS

Figure 7:
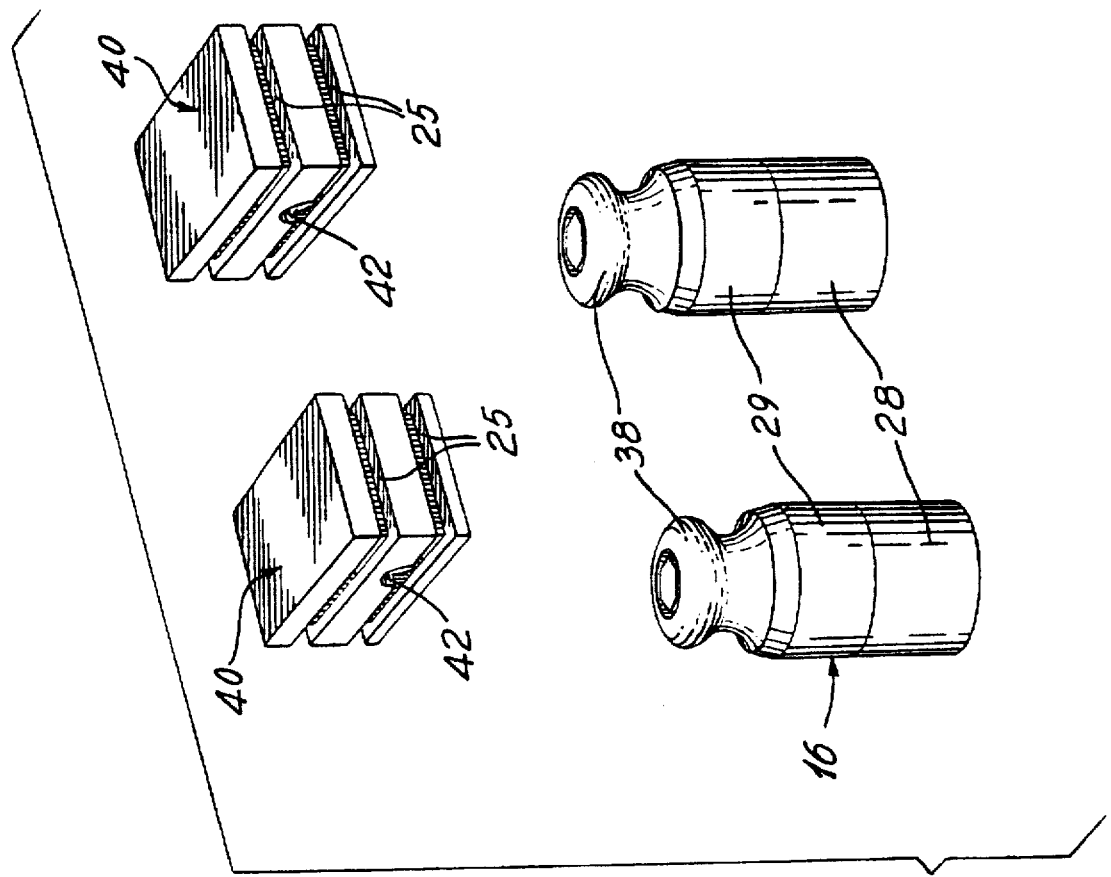
FIG. 7 illustrates a kit in accordance with the present invention.

Referring now to the drawings, FIG. 1 shows an embodiment of the present invention in which a denture 10 is shown placed above a mandible 12. The mandible 12 is shown with a gum 14 in which endosseous implants 16 and 18 are provided.

As shown in FIGS. 5, 6, each endosseous implant abutment 16 includes a pin 28 which is anchored in the osseous material 30 of the gum 14. A second part 29 is mounted on pin 28 and is retained by hollow bolt 35 in recess 34. A complementary cylinder 40 having a recess defining a female seat 26, for receiving the implant abutment 16, is located in the denture 10.

In the embodiments shown in FIGS. 3 through 7, there is illustrated the endosseous implant abutment 16 provided with a locking means. A pin having parts 28 and 29 is also provided which is anchored in the osseous material 30 of gum 14, and a head 38 is mounted to the pin part 29 with the bolt 36. Head 38 is provided with an arcuate annular recess or groove 44. The companion cylinder 40 is provided with a tangential bore 42 to the seat 26. When the cylinder 40 is mated to the head 38, the bore 42 coincides with the groove 44 to provide an uninterrupted circular bore. A plunger 46 is provided in the cylinder 40 and is adapted to slide in the bore 42. A spring 48 may be located in the bore 42 at the end thereof. The head of plunger 46 is also spherical in order to permit rotation of the cylinder 40 on the head 38.

Figure 4:
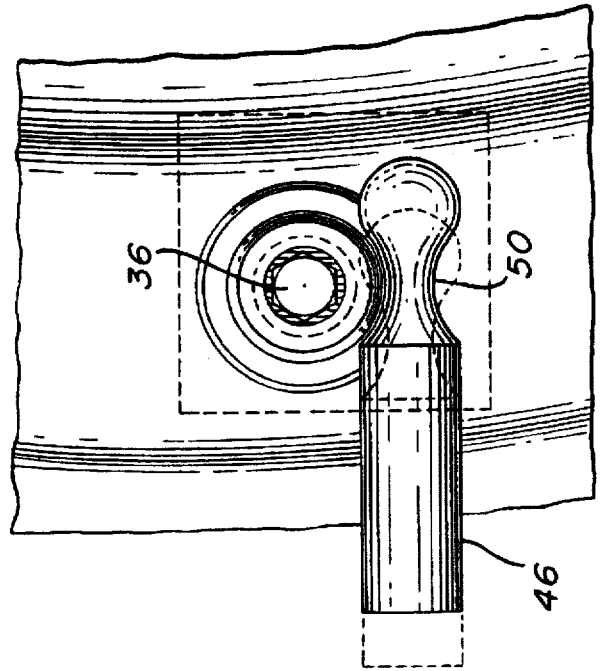
FIG. 4 is a fragmentary enlarged top plan view, partly in cross-section, of a detail of the present invention.

The locking of the cylinder 40 on the head 38 is illustrated in FIGS. 4, 5 and 6 and occurs when the cylinder 40 is seated on the head 38 with the bore 42 in tangential alignment with the groove 44. The plunger 46 is provided with an arcuate recess 50. When the arcuate recess is not aligned with the head 38 and the spherical head of the plunger 46 intersects the groove 44 and the bore 42, the cylinder 40 is thus locked. When it is desired to release the cylinder 40 from the head 38, the plunger 46 is pressed against the urging of the spring 48 so that the arcuate recess 50 coincides with the groove 44. The diameter of the recess 50 is such that the top portion of the head 38 will be accommodated in the recessed portion. In such a position, the plunger 46 does not present an obstacle, and thus the cylinder 40 can be removed or placed onto the head 38.

Cylinders 40 are rectilinear and in fact have a rectangular cross-section as shown with grooves 25 to better anchor the cylinders in the denture 10. These cylinders can take up any shape which will resist torquing forces once embedded.

In operation, a kit of two locking implant abutments 16, as shown in FIG. 8, would be provided along with two locking cylinders 40. First, the implant abutments 16 would be inserted by conventional implanting procedures into the gum 14 of either the maxilla or mandible 12 in the embodiment shown. In the present embodiment, two endosseous implants 16 are located towards the front of the mandible in the approximate positions of the last canine teeth. Thus, in the present embodiment, two implants are located on the mandible to support a denture.

A denture 10 would then be formed including an artificial gum 20 made of acrylic material with simulated teeth 22 projecting therefrom, as shown in FIG. 1. The artificial gum 20 would be formed after taking the necessary impression of the mandible 12 after the implants and abutment 16 have been placed on the mandible 12. At each location of an impression of an abutment 16, cylinders 40 would be placed to be embedded in the denture 10 being formed. Care would be taken to ensure that each individual cylinder 40 is in axial alignment with its respective implant abutment 16. The cylinders 40 would be located corresponding to the implant abutment 16. As can be seen, even if the implant abutments 16 are not exactly parallel in terms of their respective axes, each cylinder 40 may be independently aligned and located in respect of its respective implant. Thus, when it is necessary to place the denture 10 on the mandible 12, each seat 26 and the respective cylinder 40 will nest on a respective implant 16.

The provision of the frusto-spherical seats and heads allows for easy location and fitting of the denture 10. Although a frusto-spherical seat and head will not provide a secure fit, the locking means provided by implants 16 and cylinders 40 will secure the denture 10 to the implants.

Two implants, and corresponding cylinders would be necessary to secure a denture. The support against the forces applied to the teeth during function is absorbed by the abutments and by the residual gum tissue. The present embodiment shows two such implants and cylinders.

The implants could be formed in one piece although the embodiment shown in the drawings shows separate heads being bolted to the ends of the endosseous elements.

We claim:

1. A dental prosthesis kit consisting of two implant abutments adapted to be located in spaced-apart positions on the gum of at least one of the mandible or maxilla, wherein the two implant abutments define an axis, each implant abutment including an end which is adapted to be exposed from the gum when installed, wherein the end defines a male member having at least a frusto-spherical form, two separate rigid seat members adapted to be embedded in the artificial gum of a dental prosthesis and each seat member including a body defining a female seat adapted to receive said at least a frusto-spherical male member of the one of said implant abutments, said seat members adapted to be in alignment with the male members of said abutments such that when the prosthesis is fitted on the implant abutments, the female seats will sit on the male implant abutments and can rotate on said implant abutments about said axis, and locking members are provided within the seat members, each locking member including a sliding pin having a spherical head slidable in said female seat between a locking position where the spherical head is adapted to interfere with the one of said male members in order to lock the female seat and therefore the prosthesis to the implant abutment while allowing limited rotation of the prosthesis about said axis and a release position clear of the one of said male members, said sliding pin adapted to extend outside the prosthesis for manual engagement of the pin to selectively release or lock the prosthesis when the prosthesis is mounted to the implant abutments.

2. A prosthesis kit as defined in claim 1, wherein the implant abutments are in the form of elongated posts adapted to be implanted in the osseous material of either mandible or maxilla, and the elongated posts are provided with an exposed end in the form of a frusto-spherical head.

3. A prosthesis kit as defined in claim 2, wherein the frusto-spherical head is in the form of a separate member which can be fastened to the end of the post.

4. A dental prosthesis kit as defined in claim 1, wherein the sliding pin has a circular cylindrical body terminating in said spherical head and defining a narrow arcuate annular groove between the head and the body of the sliding pin, each seat member including a bore extending tangentially of the female seat such that it intersects the female seat in a chordal manner, the circular cylindrical sliding pin sliding in the bore between the locking position and the release position.

5. A method of providing for a mechanical attachment of a denture to either the mandible or maxilla which includes providing two spaced-apart implant abutments in the gum of a patient defining an axis of rotation between each implant abutment and each abutment having an exposed male member of at least a frusto-spherical shape, selecting two rigid seat members which match with the respective male members of the implant abutments, preparing a denture by taking an imprint of the gum with the implant abutments, molding denture gum material to the imprint of the gum with the implant abutments, embedding the seat members in the denture gum material such that each respective seat member is aligned and is adapted to sit on the exposed male member of each implant abutment and ensuring that the two implant abutments and seat members have locking means for securing the denture to the implant structure while providing rotation of the prosthesis during mastication.

6. The method of claim 5, wherein said locking means includes a sliding pin having a spherical head.

7. A dental prosthesis kit consisting of two implant abutments adapted to be located in spaced-apart positions on the gum of at least one of the mandible or maxilla, wherein the implant abutments define an axis of rotation between them, each implant abutment including an end which is adapted to be exposed from the gum when installed, wherein the end has at least a frusto-spherical form defining a male member, two separate rigid seat members adapted to be embedded in the artificial gum of a dental prosthesis and each seat member including a body defining a female seat adapted to receive the at least a frusto-spherical male member of the implant abutment, said seat members adapted to be in alignment with each implant abutment such that when the prosthesis is fitted on the implant abutments, the female seats will sit on the exposed male implant abutments, and locking members are provided within the seat members, each locking member including a sliding pin having a spherical head slidable in said seat member between a locking position where the spherical head interferes with the respective at least a frusto-spherical male member in order to lock the seat member thereto and therefore the prosthesis to the implant abutment and a release position where the sliding pin is clear of the male member, said sliding pin adapted to extend outside the prosthesis for manual engagement of the pin to selectively release or lock the prosthesis when the prosthesis is mounted to the implant abutments, the improvement wherein the seat member has a female seat surface, and wherein the sliding pin is adapted to slide in a bore in the seat member, the bore having an axis tangential to the female seat surface such that it intersects the female seat surface in a chordal manner, the sliding pin being adapted for reciprocal sliding movement in the bore biased by a spring, and the male member of the implant abutment including an arcuate concave groove which coincides with the bore in the seat member when the female seat surface is fitted thereon to allow the sliding pin and spherical head to slide therein, wherein the interference in the arcuate concave groove of the male member with the spherical head of the sliding pin provides locking of the seat member on the implant abutment while providing a rotation of the prosthesis about said axis during mastication.

* * * * *